United States Patent

Lesny et al.

[11] Patent Number: 5,383,465
[45] Date of Patent: Jan. 24, 1995

[54] ULTRASONIC INSTRUMENT

[76] Inventors: Jan Lesny, Tarrants, Stoborough, Wareham, Dorset BH20 5AJ; Joseph D. Aindow, 6 High Street, Sydling, Dorchester, Dorset DT2 9PB, both of Great Britain

[21] Appl. No.: 861,900
[22] PCT Filed: Dec. 18, 1990
[86] PCT No.: PCT/GB90/01977
§ 371 Date: Aug. 11, 1992
§ 102(e) Date: Aug. 11, 1992
[87] PCT Pub. No.: WO91/08706
PCT Pub. Date: Jun. 27, 1991

[30] Foreign Application Priority Data

Dec. 18, 1989 [GB] United Kingdom ............... 8928533

[51] Int. Cl.$^6$ ............................................. A61B 8/06
[52] U.S. Cl. ............................................. 128/662.05
[58] Field of Search ................... 128/660.1, 661.01, 662.05–662.06

[56] References Cited

U.S. PATENT DOCUMENTS

| | | | |
|---|---|---|---|
| 2,507,770 | 5/1950 | Claassen | 310/322 |
| 3,556,079 | 1/1971 | Omizo | 128/662.05 |
| 4,249,539 | 2/1981 | Vilkomerson et al. | 128/662.05 |
| 4,534,221 | 8/1985 | Fife et al. | 128/661.01 X |
| 4,706,681 | 11/1987 | Breyer et al. | 128/642 |
| 4,887,606 | 12/1989 | Yoch et al. | 128/662.05 |
| 4,911,172 | 3/1990 | Bui et al. | 128/662.06 |
| 5,186,177 | 2/1993 | O'Donnell et al. | 128/661.01 X |

FOREIGN PATENT DOCUMENTS

| | | |
|---|---|---|
| 260953 | 3/1988 | European Pat. Off. . |
| 3718604 | 12/1988 | Germany . |
| 2157828 | 10/1985 | United Kingdom . |

OTHER PUBLICATIONS

Fukutome, T. et al "Puncturing Apparatus", Europ. Pat Applin. Publ. #EP0190719 Publ. Aug. 1986.
Extract found on p. 169 of "Engineering" Journal, Mar. 1983.

*Primary Examiner*—Francis Jaworski
*Attorney, Agent, or Firm*—Fields, Lewis, Rost & Smith

[57] ABSTRACT

An ultrasonic invasive instrument such as a biopsy needle has an ultrasonic transducer mounted at one end, with the transducer being electrically coupled to two conductors such as a stylet and central cannula forming the instrument body and transmitting signals from the transducer identifying the instrument's location in a field transmitted by an imaging scanner, the transducer being coupled to at least one of the conductors by an ohmic or capacitive coupling, with for example body fluids serving as the couplant material.

8 Claims, 1 Drawing Sheet

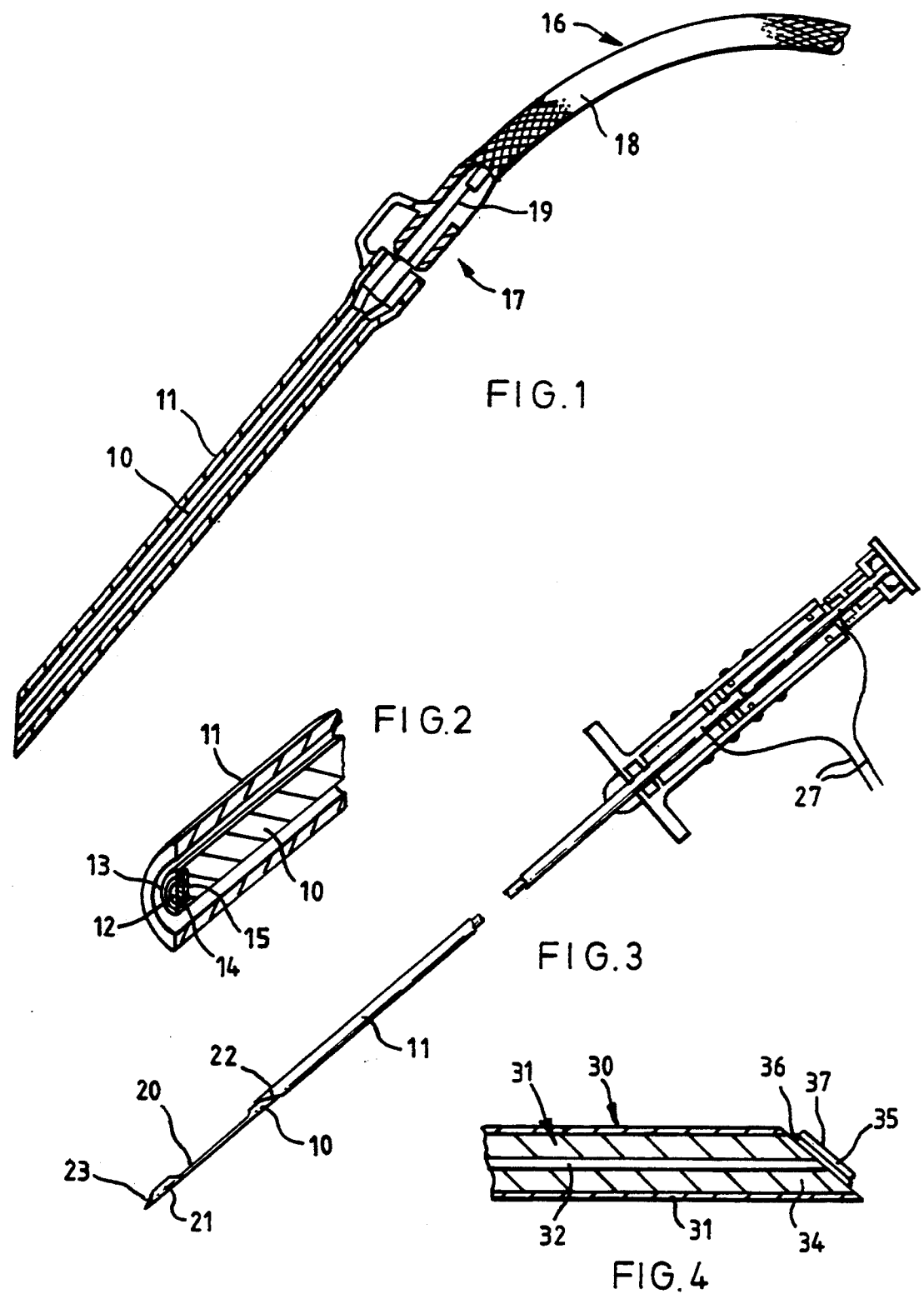

ULTRASONIC INSTRUMENT

INTRODUCTION AND BACKGROUND

The present invention relates to an ultrasonic instrument for use in interventional procedures employed in surgical and medical investigations, treatment or diagnosis, in research and in related fields.

In procedures involving the insertion of an instrument into a human or animal body, it is often necessary for the position of the instrument to be known accurately. The use of ultrasonic instruments, in particular imaging scanners, to guide the insertion of surgical instruments such as puncture needles or catheters during invasive medical procedures is known. The imaging system usually relies on detection of passive echos from the instruments, but more recently techniques have been developed in which an ultrasonic transducer is located on the end of the instrument to provide an "active" detection system. The ultrasonic wave emitted by the imaging system is detected by the transducer, and an electrical signal is conveyed back to the imaging system, or the transducer emits an ultrasonic signal for detection by the imaging system. For more general information reference can be made to U.S. Pat. No. 3,556,079 and U.S. Pat. No. 4,249,539. GB-A-2157828 describes an instrument in which the ultrasonic sensor is connected to a detection circuit by a pair of solid conductive paths. This requires quite complicated and accurate fabrication techniques.

OBJECTS AND SUMMARY OF THE INVENTION

It is an object of the present invention to provide an ultrasonic invasive instrument where the fabrication can be significantly less complicated and therefore less costly.

It has been found unexpectedly that it is not essential to have a conductive or very low resistance, connection to the transducer, but that satisfactory performance can be made if an ohmic or capacitive coupling is used.

According to the invention there is provided an ultrasonic invasive instrument comprising a device having an ultrasonic sensor secured at or near a first end of the device which is inserted into the body, and two electrically conductive paths extending from the sensor to a second end of the device for connection to the electronic circuitry, the sensor having first and second electrode surfaces, at least one of which surfaces is electrically connected to a respective conductive path by an ohmic or capacitive coupling.

More particularly the invention is applied to a biopsy probe in which an electrically conductive stylet is arranged to be surrounded by an electrically conductive cannula. An electrically insulating barrier, such as an electrically non-conducting polymer film is positioned between the outer surface of the stylet and the inner surface of the cannula, and the ultrasonic sensor is mounted on the remote end of the stylet and, in use, is electrically coupled by body fluids or the like to the cannula so that signals generated by the sensor can be detected by an electronic circuit connected across the near ends of the stylet and the cannula.

The electrical connection between the stylet and sensor may be a capacitive and/or an ohmic coupling.

The coupling between the sensor and the needle may be a capacitive and/or an ohmic coupling, the latter being provided by the medium present in use adjacent the sensor.

Thus the invention provides a construction for an invasive ultrasonic instrument which is easier to manufacture than the instrument of, for example, GB-A-2157828.

The invention is applicable to a wide range of instruments used in surgical and medical investigations, diagnosis, treatment and associated research, for example puncture needles, catheters and endoscopes, used for example for aspiration of liquids, taking histological and cytological biopsy samples, chorionic villus sampling, umbilical cord blood sampling, amniocentesis, in vivo fertilisation, positioning capsules for taking small bowel biopsies, ductography, selective arteriography, phlebography, embolisation, drug administration, radioactive source implantation and cardiac catheterisation.

Other aspects, preferred features and advantages of the invention will be apparent from the following description and the accompanying claims.

DESCRIPTION OF THE DRAWINGS

The invention will be further described by way of example with reference to the accompanying drawings, in which:

FIG. 1 shows an ultrasonic invasive instrument forming a first embodiment of the invention;

FIG. 2 shows an end of the instrument of FIG. 1 on enlarged scale;

FIG. 3 shows a biopsy needle forming a particularly preferred embodiment of the invention; and FIG. 4 shows another particularly preferred embodiment of the invention.

DESCRIPTION OF THE PREFERRED EMBODIMENTS

Referring to the drawings, in FIGS. 1 and 2 a metallic stylet 10 has an electrically insulating outer polymer coating and is surrounded by a hollow metallic cannula or needle 11. A preferred coating is parylene by Union Carbide which has FDA approval, but other medically approved coatings may be used. Alternatively, or as wall, the inner surface of the cannula may be coated. An ultrasonic sensor 12 (see FIG. 2) is bonded to the end surface 13 of the stylet 1, or it may be bonded on the side a short way from the end face. The bonding is achieved by a thin layer 15 of a conventional medically-inert adhesive, but very preferably biocompatible. The adhesive need not be electrically conductive, since it is sufficient to provide an ohmic or capacitive coupling.

The sensor is preferably a PVDF (polyvinylidene difluoride) film, which is typically 52 microns thick. Other sensors, such as lead zirconate titanate might be used. Usually, the material has a conductive metallic coating on its two major surfaces to form electrodes. However, it has been found that it is not necessary to provide these coatings and it is particularly preferred that uncoated material be used. One advantage which this gives is that the uncoated material is transparent and so more easily positioned by eye on the stylet tip. Also, the polarity of the connection of the material (i.e. which face is electrically connected to which conductor) has been found not to be important.

The solid stylet 10 forms a first conductor and the surrrounding cannula 11 forms a second conductor for feeding signals from the sensor 12. The sensor 12 is electrically coupled to the cannula 11 by body fluids which will surround and enter the end of the cannula 11 adjacent the sensor 12. In the alternative a conductive fluid, such as saline, may be fed into the cannula 11, the fluids providing an ohmic or capacitive electrical coupling.

An outer sheath 18 and inner core 19 of a co-axial cable 16, which fits on a housing 17, are electrically connected to the near ends of the stylet 10 and the needle 11. The stylet 10 and housing 17 are removeable to allow fluids etc. to be sucked into the cannula 11. A twisted pair two-core cable may be used with a surrounding grounded sheath for improved signal to noise ratio, the wires of the twisted pair being connected respectively to the stylet 10 and cannula 11. Signals generated by the transducer 12 are transmitted along the stylet 10 and the needle 11 to be measured in effect across the near ends of the stylet 10 and the needle 11. The sensor 12 couples electrically with the stylet 10 either ohmically or capacitively, as explained above, and also couples with the needle 11 ohmically and/or capacitively. Although the signals generated by the transducer are small, the apparently poor electrical connections for the sensor 12 are in fact found to be satisfactory in practice.

The device of FIGS. 1 and 2 is typically for cytological use or a shaped end may be provided on the cannula 11 for histology.

FIG. 3, shows a biopsy needle, the particular design shown being similar to the "Tru-Cut" needle marketed by Travenol Laboratories, Inc. The stylet 10 has a recess 20 near its end 21. The recess 20 cooperates with a cutting edge 22 on the end of the cannula 11 to take a tissue sample as the stylet 10 moves back into the cannula 11, as is well known. The ultrasonic sensor may be positioned in the recess 20, but preferably is positioned on the end surface 23 as in the embodiment of FIGS. 1 and 2. In the recess 20, the sensor is better protected from damage and, in use, ultrasonic waves impinging on the remote end of the stylet 10 may be acoustically conducted up the stylet to the sensor at 16. Although this introduces a short acoustic delay, which may cause a registration error in the image, this may be clinically insignificant. If required this delay may be corrected for by a suitable signal processing method in the associated electronic detection and display circuitry. A greater problem arises when the probe is positioned in the body with the stylet 10 withdrawn into the cannula 11. Body fluids are needed to electrically couple the sensor 12 to the cannula 11, and these might not penetrate past the end 23. Saline could be injected in the probe to reduce this difficulty, but it is particularly preferred that the sensor be mounted on the end surface 23.

The stylet 10 and cannula 11 are electrically connected to the monitoring instrumentation (not shown) by a twisted pair cable 27.

The outer surface of the stylet 10 is electrically insulated from the cannula 11 by a polymer coating. Also, as indicated above, it is possible to insulate the inner surface of the needle 11 to provide the insulating barrier between the stylet 10 and the needle 11 or a separately formed insulating sleeve could also be used in the embodiments of FIGS. 1 and 2 and FIG. 3.

FIG. 4 illustrates another embodiment, in which the probe 30 has a hollow metallic body 31, typically of stainless steel, and a copper wire 32 is carried within the hollow core 33. The wire 32 is electrically insulated from the body 31 by epoxy resin 34. A PVDF sensor 35 is bonded to the wire 32 by a U-V cured adhesive 36. As before the sensor does not need a metallic coating on its surface and the adhesive 36 need not be electrically conductive. The sensor 35 is spaced from the body 31 and its outer surface (electrode) 37 makes electrical contact with the body 31 by a capacitive or ohmic coupling, such as by body fluids. A twisted wire pair is connected to the near ends (not shown) of the body 31 and wire 32. The probe 30 may be part of a body tissue sampling device, such as the device of FIGS. 1 and 2.

Various modifications may be made to the described embodiments and it is desired to include all such modifications as fall within the scope of the accompanying claims.

We claim:

1. An ultrasonic invasive instrument comprising a device having an ultrasonic sensor secured at or near a first end of the device for insertion into the body, and two electrically conductive paths extending form the sensor to a second end of the device for connection to electronic circuitry, the sensor having first and second electrode surfaces, at least one of which surfaces is capable of being electrically connected to a said respective conductive path by an ohmic or capacitive conductive fluid.

2. An instrument as claimed in claim 1, in which the sensor is a PVDF film ultrasonic transducer.

3. An instrument as claimed in claim 2, in which the PVDF is not provided with a metallic coating on one or both of its faces.

4. An instrument as claimed in claim 1 in which the sensor is glued in position on the device with an electrically non-conducting adhesive.

5. An instrument as claimed in any one of claim 1 in which one of the electrically conductive paths is provided by a wall of the device and, in use, the sensor is ohmically or capacitively coupled to the wall.

6. An instrument as claimed in claim 5, in which the fluidic ohmic or capacitive conductive fluid is a body fluid.

7. An instrument as claimed in any one of claims 1 to 6, wherein the sensor is mounted on a cylindrical stylet and is electrically coupled to a conductor passing through the centre of the stylet, and to the cylindrical stylet wall.

8. An instrument as claimed in any one of claim 1, wherein the sensor is mounted on a stylet which provides a first of the conductive paths and the second is provided by a cannula surrounding the stylet and through which the stylet moves.

* * * * *